United States Patent [19]
Tanner et al.

[11] Patent Number: 5,468,239
[45] Date of Patent: Nov. 21, 1995

[54] APPARATUS AND METHODS FOR USING A CIRCUMFERENTIAL LIGHT-EMITTING SURGICAL LASER PROBE

[75] Inventors: Howard M. C. Tanner; James L. Sorenson, both of Salt Lake City, Utah

[73] Assignee: Sorenson Laboratories, Inc., Salt Lake City, Utah

[21] Appl. No.: 126,674

[22] Filed: Sep. 24, 1993

Related U.S. Application Data

[63] Continuation of Ser. No. 870,005, Apr. 13, 1992, abandoned.

[51] Int. Cl.$^6$ .................................................. A61B 17/36
[52] U.S. Cl. .................................. 606/15; 606/7; 606/17; 604/101
[58] Field of Search ........................... 606/17, 18, 7, 606/14, 15, 16; 604/101; 128/355–358, 4, 6

[56] References Cited

U.S. PATENT DOCUMENTS

| | | | |
|---|---|---|---|
| 4,573,966 | 3/1986 | Weikl et al. | 604/101 X |
| 4,592,353 | 6/1986 | Daikuzono | 606/17 X |
| 4,636,195 | 1/1987 | Wolinsky | 604/101 X |
| 4,672,961 | 6/1987 | Davies | 606/18 X |
| 4,768,858 | 9/1988 | Hussein | 606/7 X |
| 4,875,897 | 10/1989 | Lee | 606/17 X |
| 4,934,340 | 6/1990 | Ebling et al. | 128/4 X |
| 4,946,440 | 8/1990 | Hall | 606/7 X |
| 5,026,366 | 6/1991 | Leckrone | 606/7 |
| 5,190,538 | 3/1993 | Hussein et al. | 606/17 |
| 5,242,438 | 9/1993 | Saadatmanesh et al. | 606/17 X |
| 5,254,112 | 10/1993 | Sinofsky | 606/17 X |

*Primary Examiner*—Peter A. Aschenbrenner
*Attorney, Agent, or Firm*—Workman Nydegger Seeley

[57] ABSTRACT

Novel apparatus and methods for a circumferential laser and methods for using a circumferential burning laser are disclosed. The circumferential burning laser comprises a conical surface at the distal end of a probe of the laser which is coated with a highly reflective material such as gold. The conical, reflective surface is designed so as to direct the laser light which is emitted through the interior metal lumen of the laser probe so that the laser light is redirected perpendicular to the longitudinal axis of the laser probe. This is in contradistinction to the typical laser probe wherein the laser light is directed longitudinally through the end of the laser probe. The laser light is provided by a carbon dioxide laser which is attached at the proximal end of the laser probe.

The present invention also comprises methods for using a circumferential burning laser. The methods for using a circumferential burning laser involve placing the above-described laser probe in position relative to a target site. In the preferred embodiment, the laser probe is placed in the urethral canal such that a transurethral resection of benign prostatic hypertrophy may be performed.

44 Claims, 9 Drawing Sheets

APPARATUS AND METHODS FOR USING A CIRCUMFERENTIAL LIGHT-EMITTING SURGICAL LASER PROBE

This application is a continuation of U.S. application Ser. No. 870,005, filed Apr. 13, 1992, for APPARATUS AND METHODS FOR USING A CIRCUMFERENTIAL LIGHT-EMITTING SURGICAL LASER PROBE, now abandoned.

BACKGROUND

1. The Field of the Invention

The present invention relates to apparatus and methods for an improved type of surgical laser device. In particular, the preferred embodiment of the invention relates to apparatus and methods for a surgically designed, carbon dioxide laser probe which provides a laser light emission that is polarized in a circumferential relation about the distal treatment end of the surgical laser probe. This circumferential emission of laser light results in up to about a 90% efficient use of light energy emitted from a carbon dioxide laser light generator.

2. The Background Art

The three types of lasers in common surgical use are the carbon dioxide, argon and Nd:YAG (neodymium-doped yttrium-aluminum-garnet) laser, each named after the lasing medium employed. The carbon dioxide laser has a wavelength of 10.6 microns and its light is invisible. This type of laser is absorbed by water. Since cells contain a high percentage of water, this laser is effective in tissue ablation because of rapid cell vaporization in a fine line.

The argon laser has a wavelength of 0.44–0.52 microns and its light is blue-green. This type of laser is absorbed by red surfaces including a thin layer of bright red blood, and is effective for coagulating small blood vessels or ablating superficial vascular lesions. This laser can be focused onto the end of, and transmitted via, a quartz fiber encased in a protective Teflon or polyethylene catheter. There is space around the quartz fiber through which gas or liquid can be directed at a target site. The laser exits the tip of the catheter with a conical distribution and a divergence angle of 7°–20°.

The Nd:YAG laser has a wavelength in the near-infrared range and is therefore invisible. This type of laser is not as well absorbed as is the argon laser, and therefore penetrates three to five times more deeply into tissue. Because of this deeper penetration, a larger volume of tissue is heated, and therefore more power is required to raise the tissue temperature to adequately heat and coagulate protein. The deeper penetration of the Nd:YAG laser makes it very effective hemostatically, but it can also result in deeper injury to underlying tissue.

The pathologic conditions amenable to treatment by these conventional lasers are diverse, but include urethral stricture disease. Obliteration of the adenomous tissues common to the pathologic conditions is accomplished through thermal coagulation by use of the Nd:YAG and argon ion lasers. Argon-pumped dye lasers are capable of treating adenomous tissues by destroying the cells of the tissue through cytotoxic photochemical reactions generated in the presence of a photosensitizer, such as hematoporphyrin derivative. The power output of the latter type of laser is insufficient to thermally destroy adenomous tissue under treatment.

Intravesicle chemotherapy, i.e., repeatedly instilling cytotoxic chemotherapeutic agents into a diseased area constitutes a second-line mode of therapy when resection fails to control recurrences of adenomous tissues. The latter form of therapy controls recurrences in approximately twenty-five to 45% of the cases, but involves multiple catheterizations, extending over a period of up to two years, with weekly catheterizations required during the first six weeks of therapy.

In the treatment of diseased areas characterized by the presence of adenomous tissue, recurrent modes of laser treatment by conventional techniques have proven ineffective for the elimination of recurrence of the disease after treatment, as compared with other forms of conventional therapy of the type described above. The Nd:YAG laser is suitable for treating selected patients with urethral stricture disease as outpatients, but may not be cost effective primarily due to the high cost of the laser system required. Argon pumped dye lasers require the presence of a photosensitizer to generate a cytotoxic photochemical reaction in order to destroy cells of adenomous tissue. A potential advantage of this form of surgery is that the cells of the tissue will be destroyed selectively because of the preferential absorption and/or retention of the photosensitizer by the cells of the adenomous tissue.

To date, it appears that well differentiated adenomous tissue areas respond poorly to the latter form of therapy. Also, hematoporphyrin derivative, the most widely used photosensitizer, is retained by the skin for approximately two to four weeks and thus require a patient to avoid direct sunlight for at least a four-week period of time. Retreatments, if frequent, become vexing to a patient.

The carbon dioxide laser overcomes many of the shortcomings of the other types of above-discussed lasers. For example, the carbon dioxide laser enables laser ablated areas to heal with a minimal amount of scar formation, does not require a photosensitizer to effect its cytodestructive effects, and is substantially less expensive than the Nd:YAG or argon ion laser systems of equivalent power output.

The use of carbon dioxide lasers, however, involves focusing a large amount of incident laser energy directly onto one point. Any laser energy not focused is randomly discarded to the surrounding environment as by-products in the form of heat and light. Because the concentration of a large amount of laser energy from carbon dioxide lasers has not been accomplished, much of the laser energy from carbon dioxide lasers is lost, and their efficiency minimized. It has been that use of carbon dioxide lasers results in a 100% power emission from which one is able to only use about 3% to 15% of the power generated by the laser. Thus, although the use of carbon dioxide lasers could be effective for the transurethral resection of adenomous tissues in urethral stricture diseases, such use of prior carbon dioxide lasers would be inefficient in terms of net power available for certain surgical procedures.

Additional shortcomings associated with the surgical laser prior art include inadequate stearability of laser light during surgical procedures. This point is emphasized during the transurethral resection of benign prostatic hypertrophy in a patient where all of the adenomous tissue cannot be adequately reached. It may be difficult for a surgeon to maneuver the handle of a laser probe in a narrow channel such that laser light is directed to a specific target. Moreover, surgeons have complained that any movement of laser devices during the transurethral resection of benign prostatic hypertrophy could cause damage to the prostatic sphincter muscles.

Some attempts have been made in the art to provide for angled laser light such that movement in the urethral canal is minimized. Such angled laser light has been demonstrated by the use of a lens to focus laser light to a point in a plane at right angles to the longitudinal axis of the laser device. This type of angled laser light, however, has not been entirely satisfactory in all situations.

Although in the angled configuration laser light is directed in a plane away from the plane normally followed by the laser device, the laser light is merely directed in another area. Therefore, if a number of areas are to be exposed to the laser light, the laser device must be manipulated in a rotational fashion so that the laser light can be directed at the various target sites. Such a procedure is not only time-consuming, but involves a risk to a patient due to the large amount of movement of a surgical tool within a patient's body.

In light of the foregoing, it is clear that many problems presented in the laser device area have not been solved. There is a need for a laser device which could solve these additional problems not remedied by currently known laser devices.

BRIEF SUMMARY AND OBJECTS OF THE INVENTION

The present invention seeks to resolve the problems incident to the use of surgical lasers as noted above. More specifically, the apparatus and methods of this invention constitute an important advance in the art of surgical laser devices by providing a laser light emission that is polarized in a circular form about the laser device. This circumferential emission results in approximately a 90% efficient use of laser light emission from the laser device.

One object of the present invention is to provide an apparatus for a circumferential laser emission and methods for using a circumferential laser emission wherein laser light is simultaneously, alternately, or intermittently directed circumferentially about a laser probe to affect many target sites.

Also, it is an object of the present invention to provide an apparatus for a circumferential laser emission and methods for using a circumferential laser emission wherein laser light is simultaneously directed circumferentially about a laser probe to affect many target sites without resorting to the continuous movement of a laser probe which could unnecessarily injure a patient.

Additionally, it is an object of the present invention to provide an apparatus for a circumferential laser emission and methods for using a circumferential laser emission wherein laser light is simultaneously redirected circumferentially about a laser probe in an energy-efficient manner.

Still another object of the present invention is to provide apparatus and methods which will improve surgical procedures directed to the transurethral resection of benign prostatic hypertrophy and other intracavity procedures within an organic body.

Further still, an object of the present invention is to provide apparatus and methods wherein the sphincter muscles of the prostatic urethra are protected during a typical transurethral resection procedure.

Additional objects and advantages of the invention will be set forth in the description which follows or may be learned by the practice of the invention.

To achieve the foregoing objects, and in accordance with the invention as embodied and broadly described herein in the preferred embodiment, a special tip is provided in a laser probe which has a conical surface at the distal end of the probe which is coated with a highly reflective material such as gold.

The conical, reflective surface is designed so as to direct the laser light which is transmitted along the interior lumen of the laser probe so that the laser light may be redirected substantially perpendicular to the longitudinal axis of the laser probe. This redirection is in contradistinction to the typical fiber optic laser probe wherein the laser light is directed longitudinally through the end of the laser probe. The laser light is provided by a carbon dioxide laser light generator which is attached at the proximal end of the laser probe.

The laser probe is moved to a fixed position relative to a target area by a placement device. The placement device is a tubular component through which the laser probe may slide. The placement tube has inflatable cuffs to support the laser probe within the target area and to isolate the target area from surrounding body tissues. The cuffs may be inflated and cooled by fluids traveling along lumens in the placement tube communicating between the inflatable cuffs and the area exterior to the laser probe.

The present invention also comprises methods for using a circumferentially burning laser apparatus. The methods for using a circumferentially burning laser apparatus involve placing the above-described laser probe embodiments in position relative to a target site. In the preferred embodiment, the laser probe is placed via the placement device in the prostatic urethral canal such that a transurethral resection of benign prostatic hypertrophy may be performed.

Once the laser probe is in place, the carbon dioxide laser light generator is attached at the proximal end of the laser probe. The carbon dioxide laser light generator provides the donut mode, $TE_{\phi 1}$ emission, which is employed to affect the transurethral resection. Other types of lasing media may also be employed.

The laser emission is then redirected by the tip of the laser probe such that it is directed in a circumferential fashion in a plane substantially perpendicular to the plane in which the laser probe exists. The light is redirected away from the laser probe to the targeted tissue which must be resected.

Finally, the targeted tissue is ablated by the impacted laser light and heat thereon, and the laser probe is removed from the transurethral channel. The procedure may include a further step of washing and cleaning the channel of the ablated adenomous tissue impacted by light and heat. Also, the procedure may include the step of cooling the laser probe as the operation occurs such that a critical temperature is not reached which may adversely affect a patient.

BRIEF DESCRIPTION OF THE DRAWINGS

In order to more clearly understand the manner in which the above-recited and other advantages and objects of the invention are obtained, a more particular description of the invention briefly described above will be rendered by reference to specific embodiments thereof which are illustrated in the appended drawings. Understanding that these drawings depict only the presently understood best mode of the invention and are therefore not to be considered limiting of its scope, the invention will be described with additional specificity and detail through the use of the accompanying drawings in which.

DETAILED DESCRIPTION OF THE PREFERRED EMBODIMENTS

Figure 1:
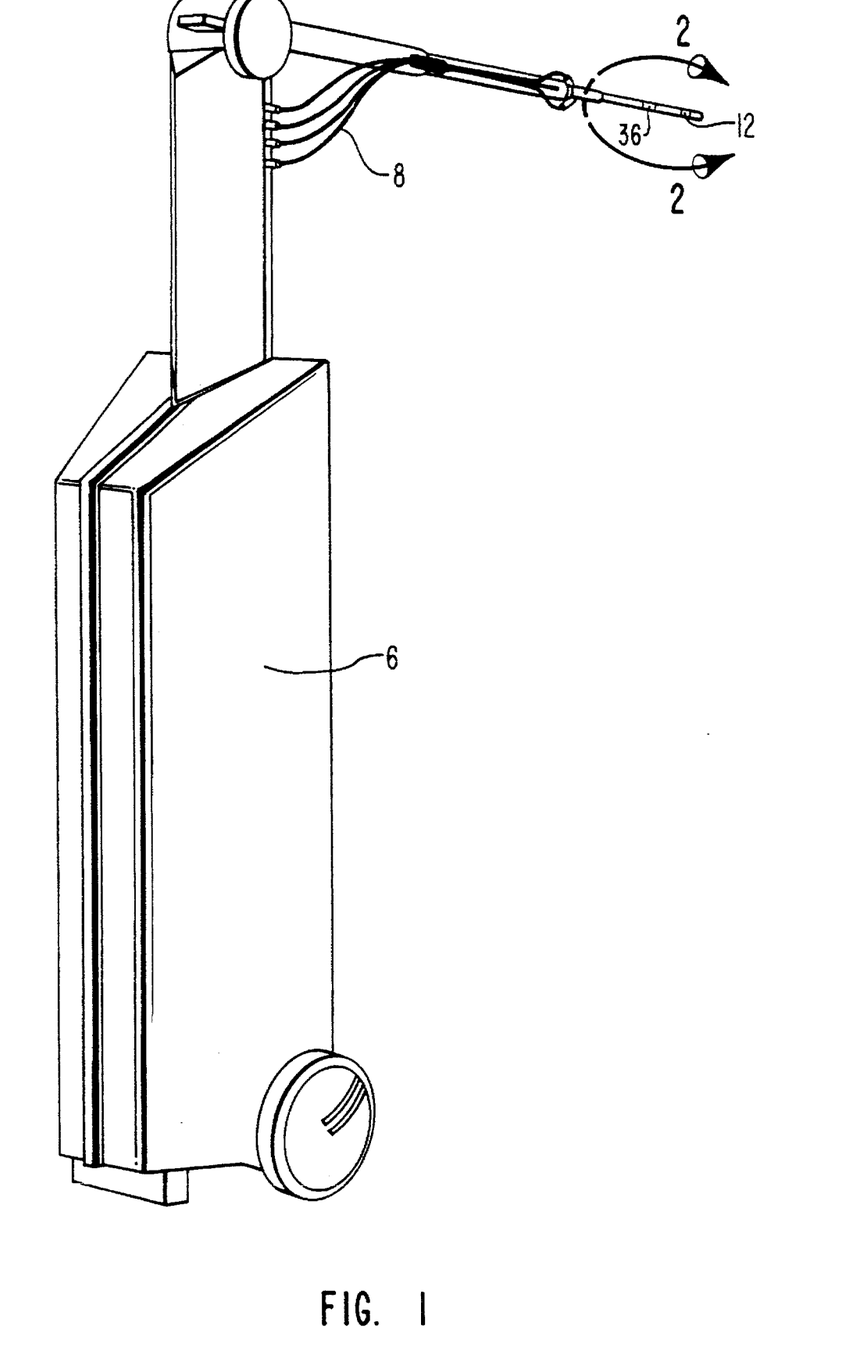
FIG. 1 is a perspective view of the present invention assembled in an operating condition to perform a transurethral resection.

The present invention can be best understood by reference to the drawings, wherein like parts are designated with like numerals throughout. The complete laser delivery system of the present invention is shown in FIG. 1. As illustrated, the laser delivery system comprises a laser light generator source 6, power, fluid and control electronics, generally designated by 8, and other apparatus, including mode generating optics (not shown), known to those skilled in the art to generate a coherent beam of light.

Figure 4:
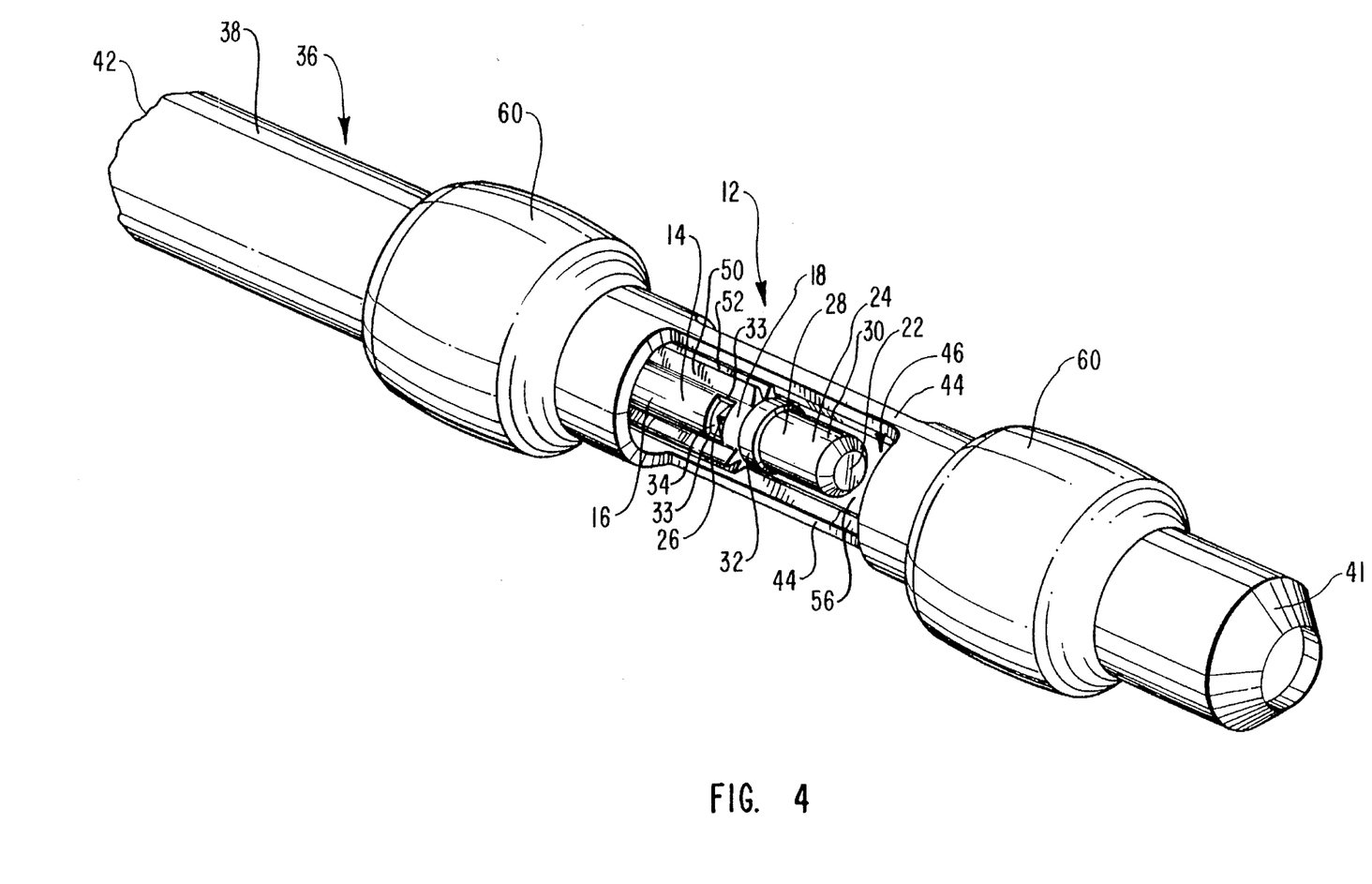
FIG. 4 is a perspective view of the laser probe within the placement device.

This laser delivery system comprises a laser apparatus or laser probe 12 for placement into a body cavity and for redirecting laser light at a target site circumferentially located about laser probe 12. Laser probe 12 is best illustrated in FIG. 4, nevertheless, the described embodiments are to be considered in all respects only as illustrative and not restrictive. Although the present invention may be embodied in other specific forms without departing from its spirit or essential characteristics, laser probe 12 is comprised of probe means for insertion and placement into the body cavity.

The probe means comprises lightguide means for guiding laser light along a pathway through the body cavity to a distal end of the lightguide means. Although the present invention may be embodied in other specific forms without departing from its spirit or essential characteristics, lightguide means comprises a lightguide 14 to guide the laser light along the pathway defined by lightguide 14. Lightguide 14 is shown in FIG. 4b, nevertheless, the described embodiments are to be considered in all respects only as illustrative and not restrictive.

Lightguide 14 extends along the body cavity to a target site, lightguide 14 defining a pathway for laser light directed therethrough. Lightguide 14 is comprised of a tube 16 having a distal end 18 and a proximal end (not shown), and as illustrated in FIG. 4b, a passage 20, preferably concentric extending therethrough. Lightguide 14 is comprised of ceramics, nevertheless, lightguide 14 may be comprised of other materials known to those skilled in the art for constructing lightguides.

As discussed, lightguide 14 acts to guide the laser light along a pathway defined by lightguide 14 to distal end 18 of lightguide 14. In the preferred embodiment of the present invention, lightguide 14 guides carbon dioxide generated laser light. Although carbon dioxide generated laser light is the preferred type of laser light, it should be understood that additional types of laser lights may be employed, such as argon or Nd:YAG.

It is also theoretically possible that in an additional embodiment, lightguide 14 may also comprise an optic fiber (not shown) to conduct laser light through lightguide 14 where permissible. The fiber (the term "optical fiber" is used in the art to define a single fiber or bundle of fibers) extends through passage 20. The fiber may be comprised of a standard light conducting material, such as a polycrystalline non-toxic metal halide material, encased in a watertight manner.

The probe means further comprises tip means, joined to and supported by the lightguide means at the distal end thereof, for redirecting the laser light so that the laser light is directed onto the target site in a direction that is defined by a selected angle of incidence relative to the pathway and that can be generally annular about substantially the entire periphery of the probe means such that the redirected laser light contacts the circumferentially located target site. Although the present invention may be embodied in other specific forms without departing from its spirit or essential characteristics, tip means comprises an elongated sleeve 24 having a substantially symmetrical reflective cone 26 attached to one end thereof, reflective cone 26 attached to the lightguide means such that the laser light strikes the reflective surface of the cone 26.

Sleeve 24 is shown in FIG. 4b, nevertheless, the described embodiments are to be considered in all respects only as illustrative and not restrictive. Sleeve 24 has a first end 28 and a second end 30. Sleeve 24 may be telescopically fitted into distal end 18 of lightguide 14, sleeve 24 having a lip 32 so that sleeve 24 will not pass through lightguide 14.

Alternatively, sleeve 24 may be attached to distal end 18 of lightguide 14 by any number of methods known to those skilled in the art. Also, it should be appreciated that distal end 18 to lightguide 14 can be configured in a variety of ways in order to be adaptable to various uses and for facilitation of the receiving of a variety of sleeves 24 of different sizes and shapes.

In a preferred embodiment of the lightguide means, second end 30 of sleeve 24 has a beveled edge 22 which encircles distal end 30 of sleeve 24. Beveled edge 22 is the first part of the lightguide means to encounter body tissue when being inserted into a generally tubular body cavity, and is beveled to reduce the likelihood that sensitive tissue will be snagged or traumatized during the insertion procedure. Although the beveled edge 22 feature of the present invention is preferred, it should be understood that this feature is not necessary to the operation of sleeve 24 for its intended purpose.

Lightguide 14 not only positions and supports sleeve 24, but also lightguide 14 selectively blocks laser light from reaching a patient. As shown in FIGS. 4 and 4b, lightguide 14 comprises members 33 which connect the distal section of lightguide 14 to the proximal section of lightguide 14. The location of members 33 between cone 26 and a target site acts to block redirected laser light from traveling therebetween.

First end 28 of sleeve 24 is configured such that reflective cone 26 is attached and laser light guided through lightguide 14 is redirected in a circumferential orientation about sleeve 24 as shown by Arrow A in FIG. 4b. Preferably, a $TE_{\phi 1}$ emission is reflected in a circumferential orientation about sleeve 24. The circumferentially redirected light passes through a window 34 in wall of lightguide 14.

As shown in FIG. 4b, cone 26 is symmetrical and proximally directed to redirect laser light from its normal course along the pathway of lightguide 14 in a manner wherein the laser light is radiated circumferentially from reflective cone 26. Cone 26 may have symmetrical, rounded sides, as in FIG. 4b, or the like. Cone 26 may have a pointed tip, a rounded tip or the like. Above all else, sleeve 24 and cone 26 may be any size or shape known to those skilled in the art such that the configuration is capable of redirecting the laser light out of its normal path so that it is virtually circumferentially emitted about cone 26.

To be capable of redirecting the laser light, cone 26 may be comprised of a reflective substance. The reflective substance may be gold-plated metal or a crafted Germanium reflector. Nevertheless, other laser light-reflective substances known to those skilled in the art may be utilized.

The present invention also comprises the step of adjusting the angle of incidence of cone 26 relative to the pathway through which the laser light is guided through lightguide 14. By adjusting the angle of incidence defined by cone 26, laser light is redirected onto the target site in a direction that is defined by the adjusted angle of incidence relative to the pathway. Although the present invention may be embodied in other specific forms without departing from its spirit or essential characteristics, the step of adjusting the angle of incidence of the surface of cone 26 comprises the step of replacing a first elongated sleeve 24 having a cone 26 with a first angle of incidence with a second elongated sleeve 24 having a cone 26 with a second, and different, angle of incidence.

Figure 5:
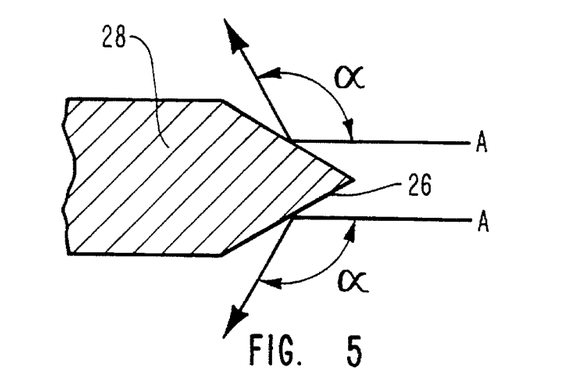
FIG. 5 is a schematic representation of the preferred embodiment of the present invention of the angle of incidence between the $TE_{\phi 1}$ laser light emission and the reflective cone area, with the angle of incidence represented by angle alpha.
Figure 5A:
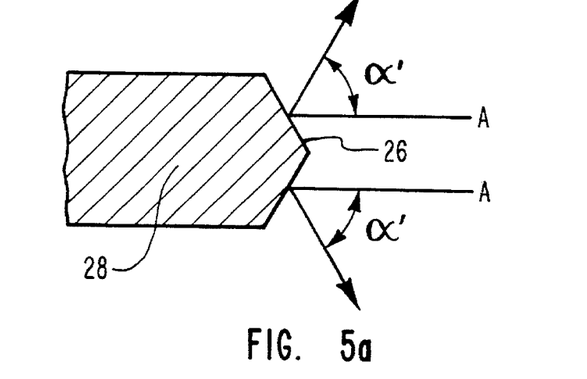
FIG. 5a is a schematic representation of another embodiment of the present invention of the angle of incidence between the $TE_{\phi 1}$ laser light emission and the reflective cone area, with the angle of incidence represented by angle alpha prime.

Cone 26 as shown in FIG. 5 is set at an angle $\alpha$ relative to the pathway through which the laser light is guided through lightguide 14. As shown in FIG. 5a, cone 26 may be tilted or adjusted to an acute angle $\alpha^1$ from the previous position of cone 26. FIGS. 5 and 5a indicate how a plurality of different cones 26 could exist, each cone 26 having a different angle of incidence relative to the pathway along which the laser light is guided. It should be remembered, however, that the described embodiments are to be considered in all respects only as illustrative and not restrictive.

The laser light will thus impinge on reflective cone 26 within a range of incident angles $\alpha$ and $\alpha^1$, respectively The illustrated tilting angle could be, of course, increased or decreased by modification to cone 26.

Since the angle of reflection is equal to the angle of incidence, the surgeon is enabled to redirect the laser light circumferentially to virtually all areas of the tissues of a patient surrounding laser probe 12. Laser probe 12 need only be advanced or retracted through the body cavity into which it is disposed in order to reach substantially all of an affected area to be treated. A surgeon need not rotate or tip a surgical instrument to direct laser light to extreme areas adjacent to the instrument.

In order for the circumferentially redirected light to pass through lightguide 14, it must be understood that lightguide 14 also comprises window means for allowing the redirected laser light to reach the target site from the tip means positioned in passage 20 of lightguide 14. Although lightguide 14 may be embodied in other specific forms without departing from its spirit or essential characteristics, window means comprise a window 34 as shown in FIGS. 4 and 4b. The described embodiments are to be considered in all respects only as illustrative and not restrictive, but lightguide 14 has two windows 34 which are formed substantially circumferentially about cone 26 so as to allow the redirected laser light to unobstructively travel between the tip means and the target site.

A novel feature of the circumferential effect of the polarized laser energy is that the laser light is reflected from cone 26 without substantially changing the character or energy level of the laser light. The circumferential laser light emission can expect to have approximately a 90% power efficiency as compared to other types of directed power emissions which achieve a power efficiency of less than 5%.

As discussed generally, the laser delivery system may also be comprised of laser light transmitting means for generating the laser light which travels along the pathway of the lightguide means through the body cavity. Although the present invention may be embodied in other specific forms without departing from its spirit or essential characteristics, the laser light transmitting means comprises a laser light generator source 6. As shown in FIG. 1, generator source 6 is attached to laser probe 12. Preferably, although not illustrated, generator source 6 is a carbon dioxide generator source 6 attached to lightguide 14.

Generator source 6 may be a source of thermal, electrical, or optical energy that provides the energy for absorption by an active medium or optic fiber. Any generator source 6 known to those skilled in the art may be utilized.

The laser light transmitting means may also comprise internal optics 8 which aid in the generation of laser light emissions, particularly a $TE_{\phi 1}$ mode emission. The laser light transmitting means may further comprise external optics (not shown) which consolidate laser light emissions, particularly a $TE_{\phi 1}$ mode emission.

All lasers, regardless of type, function in one of two operational modes. The simplest, which is the axial or Fabry-Perot mode, operates in integral multiples of two pi phase changes. A second modal permutation is the TEM or transverse electromagnetic mode. TEM modes are reproducible cyclic phase fronts which are self-propagating in any cavity in which they can reproduce in one complete round trip in that cavity.

Each of these modes is partitioned into several geometric orders. TEM lasers generate many different wavefront geometries.

It is preferred that the present invention provide a $TE_{\phi 1}$ energy transmission. This is commonly called the $TE_{\phi 1}$ in that the cross-sectional map of its energy distribution resembles a donut. It occurs because the nodes of the phasefront propagated in the laser cavity rotate with real time. Since the energy is concentrated at the circumferences of the focal spot, the beam will destroy principally the tissue at the edge of the prime focus. This type of wavefront can be useful in the preferred embodiment because of the controllable heat transfer as well as the backscatter characteristics of the $TE_{\phi 1}$ laser.

Because of the differential phasefronts and the unusual geometry of the energy envelope, the $TE_{\phi 1}$ mode of laser emission has heretofore remained virtually unutilized. Its use, however, due to the maintained high power energy levels of the present invention, provides a beam of predictably uniform power distribution. The fact that the $TE_{100\ 1}$ beam is distributed circumferentially in the preferred embodiment as illustrated in FIGS. 4b, 5 and 5a, is of benefit during the lasing of narrow channels where surgeons may simply pass a laser regressively or progressively down the channel. Surgeons need not twist or revolve a laser to reach certain tissues and risk possibly injuring sensitive tissues of a patient.

The laser delivery system may also comprise placement means for supporting laser probe 12 in the body cavity and for isolating the target site from adjacent body tissue. Although the present invention may be embodied in other specific forms without departing from its spirit or essential characteristics, the placement means comprises a placement device 36. Placement device 36 is shown in detail in FIG. 2; however, the described embodiments are to be considered in all respects only as illustrative and not restrictive.

Figure 2:
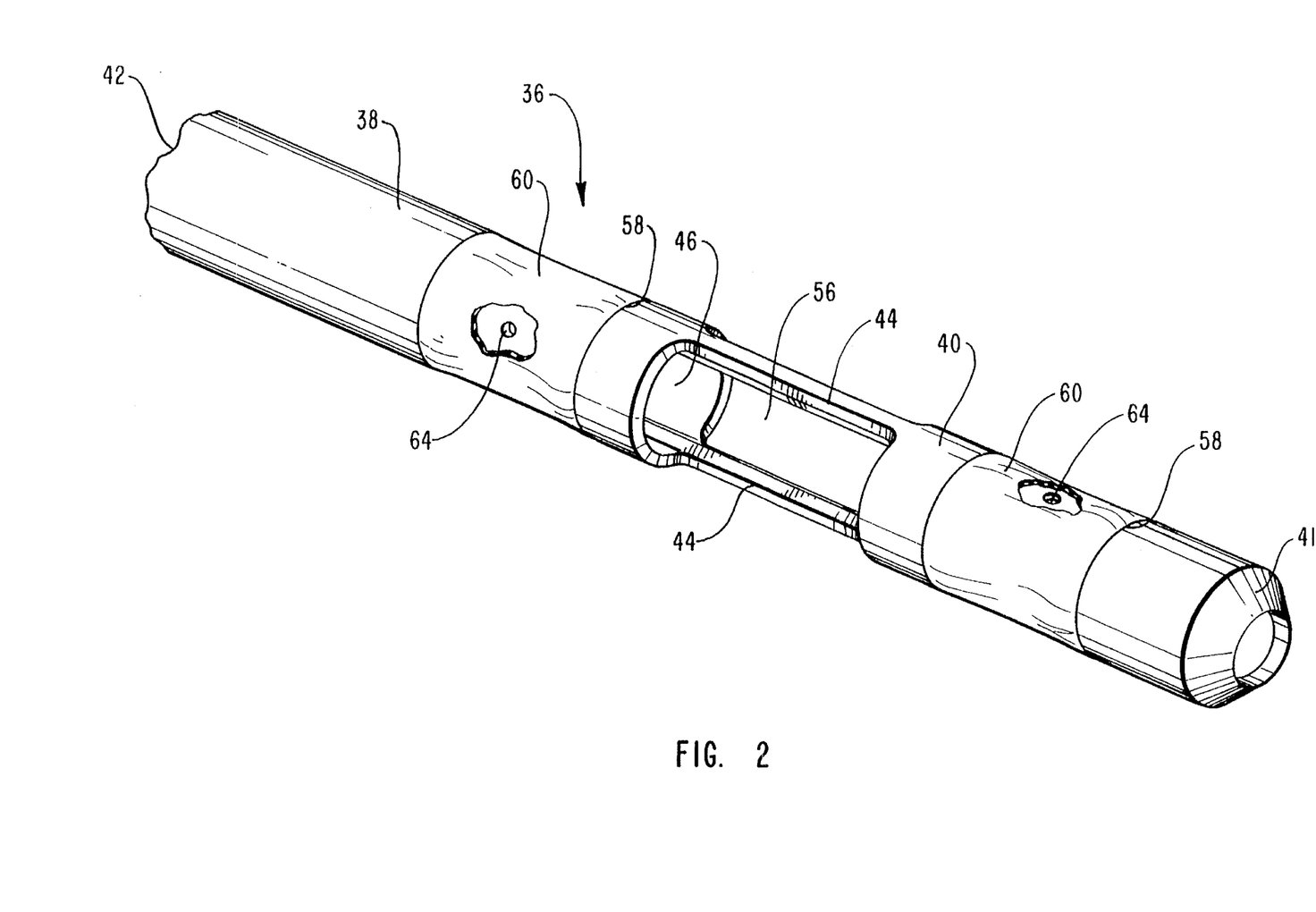
FIG. 2 is a perspective view of the placement device with the inflatable cuffs of the placement device in a deflated condition.

Placement device 36 comprises a tubular housing 38, having a distal end 40 and a proximal end 42, through which laser probe 12 is advanced or regressed, and for supporting and determining the position of laser probe 12. Placement device 36 is comprised of ceramic, plastic, stainless steel or other suitable material having an outer diameter preferably sized for insertion into or through generally tubular body cavities such as the urethra.

In a preferred embodiment of the placement device means, at distal end 40 of placement device 36 has a beveled edge 41 which encircles distal end 40 of placement device 36 Beveled edge 41 is the first part of placement device 36 to encounter body tissue when being inserted into a generally tubular body cavity, and is beveled to reduce the likelihood that sensitive tissue will be snagged or traumatized during the insertion procedure. Although the beveled edge 41 feature of the present invention is preferred, it should be understood that this feature is not necessary to the operation of placement device 36 for its intended purpose.

Placement device 36 not only positions, supports and determines the location of laser probe 12, but also selectively blocks laser light from reaching a patient. As shown in FIG. 2, placement device 36 comprises arms 44 which connect the distal section of placement device 36 to the proximal section of placement device 36. The location of arms 44 between cone 26 and a target site may act to block redirected laser light from traveling therebetween.

The external surface of placement device 36 may be suitably coated to provide thermal and electrical isolation of placement device 36 to a patient. Understandably, placement device 36 may be subject to thermal and electrical conditions which are not amenable to body tissues surrounding placement device 36. Because placement device 36 can be in direct contact with body tissues, some type of isolating or buffering means is ideally present to prevent injury to the body tissues. The isolating or buffering means are presented by the solid, plastic, or liquid coatings known to those skilled in the art of the present invention which can be applied to the external surface of placement device 36.

Figure 3:
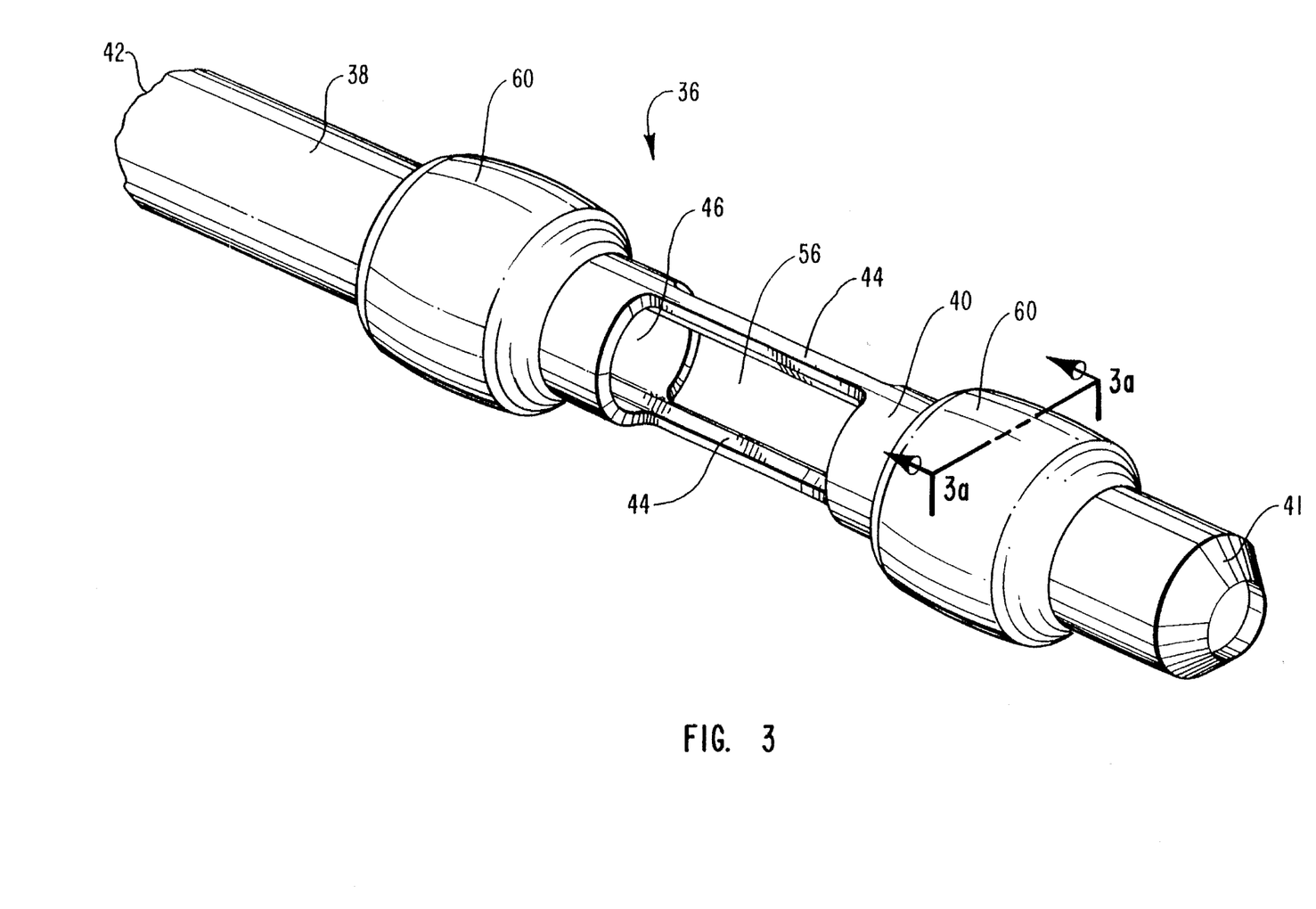
FIG. 3 is a perspective view of the placement device with the inflatable cuffs of the placement device in an inflated condition securing the placement device at surrounding tissue.

The placement means may comprise bore means for moving laser probe 12 along the placement means uninterrupted by the tissue area about the body cavity. Although the present invention may be embodied in other specific forms without departing from its spirit or essential characteristics, the bore means comprises a generally longitudinal bore 46. As shown in FIG. 2, 3, and 4, bore 46, preferably centrally located, extends along placement device 36, the bore configured such that laser probe 12 may move throughout bore 46. Nevertheless, it should be remembered that the described embodiments are to be considered in all respects only as illustrative and not restrictive.

Placement of laser probe 12 in bore 46 is conducted such that laser probe 12 travels through bore 46 to a point within placement device 36 where laser probe 12 is to be employed in a surgical procedure. Preferably, bore 46 is configured to enable laser probe 12 to be slidably positioned therein.

The laser delivery system may also comprise means for moving laser probe 12 in relation to the target site so that the laser light is directed onto the target site over a region corresponding to the distance traveled by laser probe 12. Although the present invention may be embodied in other specific forms without departing from its spirit or essential characteristics, the moving means comprise a mechanical device (not shown). Typically, laser probe 12, specifically lightguide 14, is attached to a motor driven extendable arm which advances or retracts laser probe 12 through bore 46, or simply attaches a semi-rigid line to laser probe 12 and pushes or pulls laser probe 12 into position. Other types of moving means known to those skilled in the art may also be employed to advance or retract laser probe through bore 46.

The laser delivery system may further comprise alignment means for aligning and supporting laser probe 12 within the placement means. Although the present invention may be embodied in other specific forms without departing from its spirit or essential characteristics, the alignment means comprises a track 48 along which laser probe 12 is aligned and slidably moved in relation to the target site. As an example, which is not meant to limit the scope of the present invention, illustrated in FIGS. 3a, 4 and 4a, track 48 comprises at least one longitudinally placed ridge 50 inwardly extending from the internal diameter of bore 46 which engages at least one longitudinally placed recess 52 formed along the perimeter of laser probe 12.

Figure 3A:
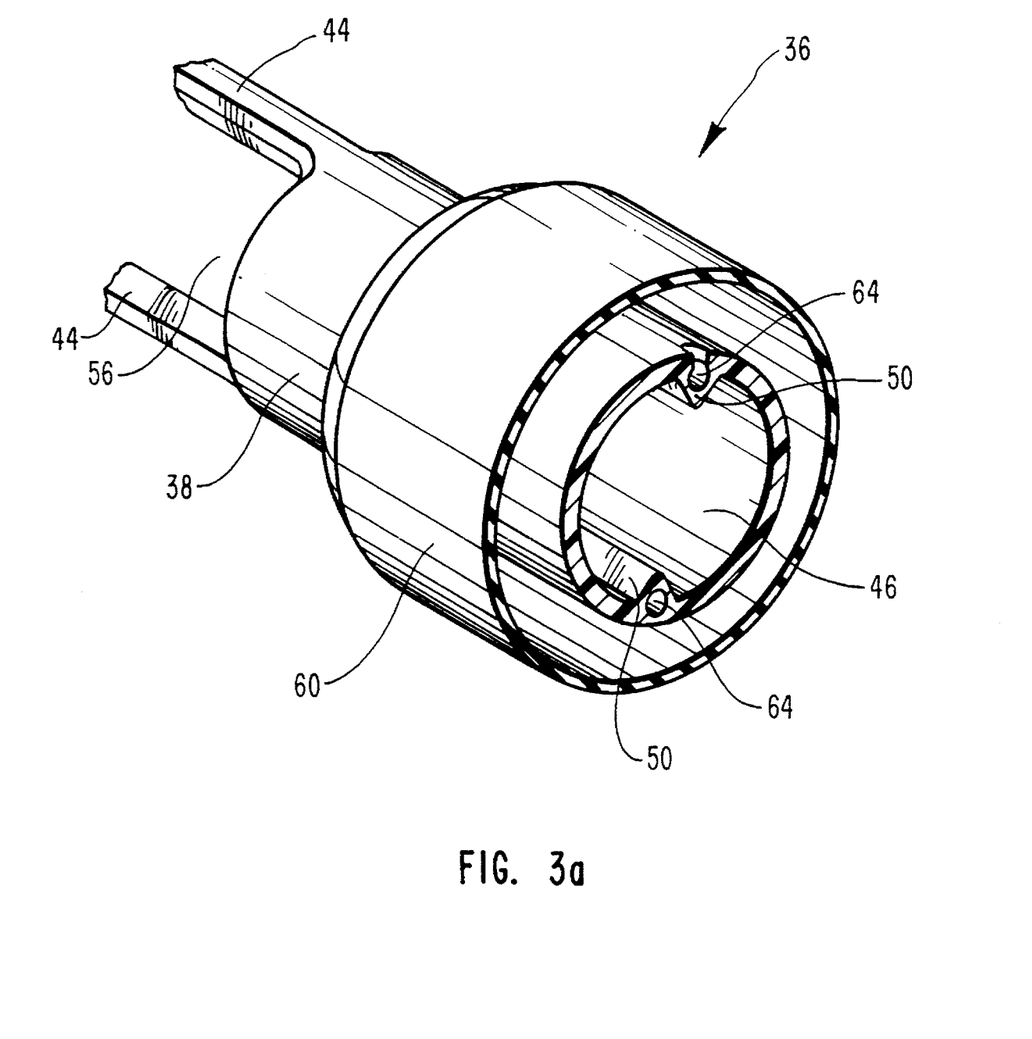
FIG. 3a is a cross-sectional view of the placement device taken along line 3a–3a of FIG. 3.
Figure 4A:
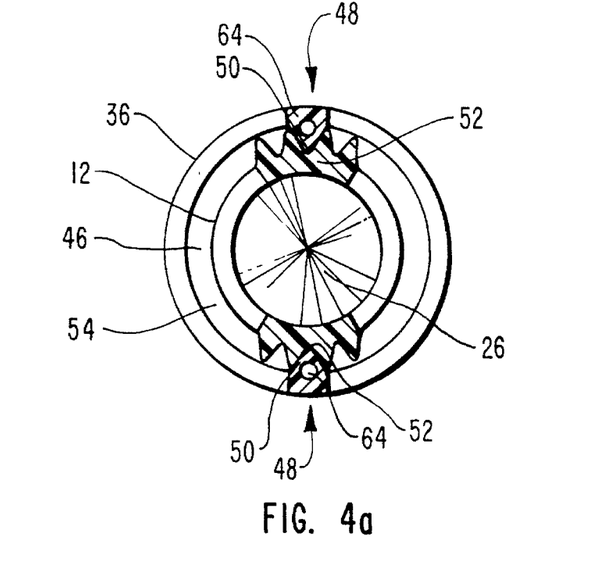
FIG. 4a is a cross-sectional view of the laser probe positioned in the bore of the placement device.
Figure 4B:
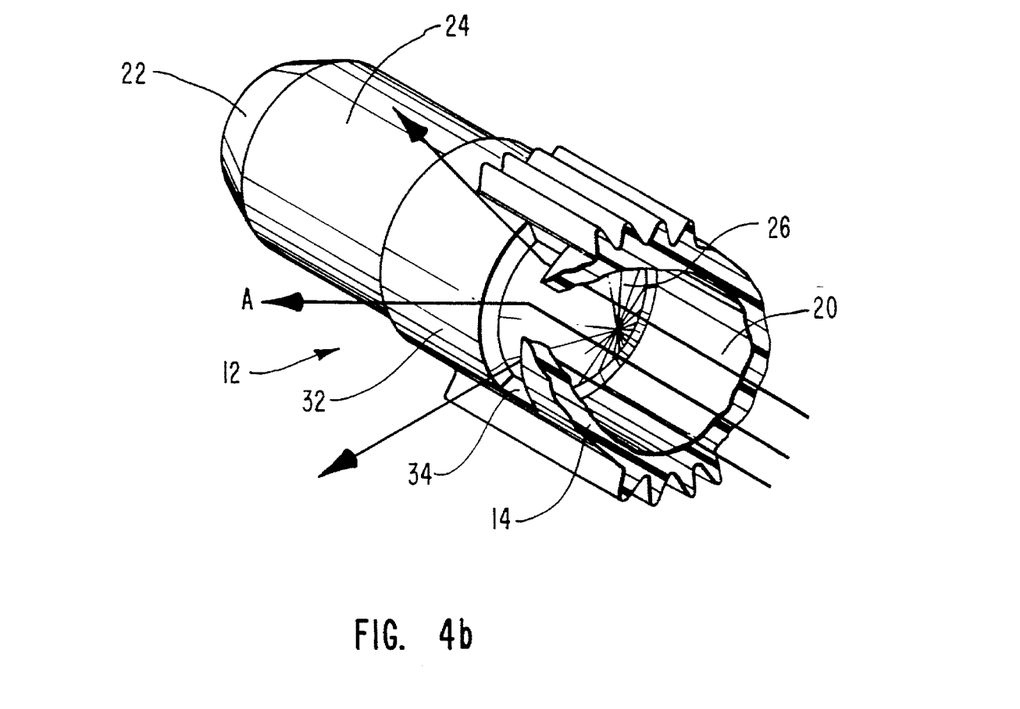
FIG. 4b is a perspective view of the laser probe broken away to indicate a coherent beam of light being circumferentially redirected about the reflective cone area of the laser probe.

As shown in FIGS. 3a and 4a, two ridges 50 are formed about bore 46 in radial displacement of about 180° (other angles of displacement may be used). Similarly, as illustrated in FIG. 4, two recesses 52 are formed about laser probe 12 in radial displacement of 180° (other degrees of displacement may be used). Further set forth in FIG. 4a, ridges 50 engage recesses 52 as laser probe 12 may be placed in proximal end 42 of placement device 36. Thus, laser probe 12 is positioned within bore 24 such that a gap 54 is between the sides of laser probe 12 and placement device 36, and no scratching, jamming, or dragging of laser probe 12 through bore 46 occurs.

Use of this type of track mechanism to move laser probe 12 through bore 46 is also preferred because laser probe 12 is aligned and supported by placement device 36. The engagement of ridges 50 and recesses 52 prevents radial movement of laser probe 12 in bore 46. This steady positioning of a surgical instrument is beneficial to surgical operations which require extreme accuracy.

Laser probe 12 is moved relative to placement device 36 such that the laser light is preferably circumferentially redirected at a urethral wall to ablate adenomous tissue areas 72 as schematically shown by the arrows in FIG. 4b, 6, and 6a–d. As laser probe 12 is moved through bore 46 in placement device 36, the laser light must be directed through placement device 36 to reach the adenomous tissue areas 72. Preferably, placement device 36 comprises window means for allowing the redirected laser light to reach the target site 72 through the placement means.

Although the present invention may be embodied in other specific forms without departing from its spirit or essential characteristics, the window means comprises at least one window 56 formed in the placement means to provide an opening between the laser light redirected from the probe means to the target site 72, unobstructed by the placement means. As an example which is not meant to limit the scope of the present invention, two windows 56 through which the circumferentially redirected laser light reaches the target site 72 from cone 26 are depicted in FIGS. 2, 3, and 3a.

The size of windows 56 allows the operator of laser probe 12 to control how much generated laser light is allowed to reach a targeted area of adenomous tissue 72. Windows 56 may be increased or decreased in size, longitudinally or radially. Although rectangular window 56 is shown in FIG. 4, different shapes may be utilized. Windows 56 are substantially radial about placement device 36 which allows substantially all of bore 46 to be exposed to the area surrounding placement device 36. Thus, when laser probe 12 is positioned within placement device 36 and laser light is circumferentially generated thereabout, windows 56 allow substantially all of the circumferentially generated laser light to contact the tissues surrounding placement device 36.

The placement means also comprises inflatable cuff means for securing the placement means to the tissue area within the body cavity. Although the present invention may be embodied in other specific forms without departing from its spirit or essential characteristics, the inflatable cuff means comprises at least one recessed area 58 along the placement means having at least one inflatable cuff 60 residing therein to secure the placement means to tissue area about the body cavity when the at least one inflatable cuff 60 is in an inflated condition.

Two cuffs 60 are shown in a deflated condition in FIG. 2 and in an inflated condition in FIG. 3. The described embodiments thereof are to be considered in all respects only as illustrative and not restrictive. Cuffs 60 are attached to placement device 36 and act to secure the position of placement device 36 relative to a target site 72. In the present situation, cuffs 60 act to secure the position of placement device 36 relative to the sphincter muscles 76 of the prostatic urethra 74.

Cuffs 60 are sized to be located at recessed areas 58 of placement device 36. As shown in FIG. 2, there are two recessed areas 58 comprising placement device 36 placed on opposite sides of window 56. Although the foregoing is preferred, the size of cuffs 60 and recessed areas 58, and the number and placement of recessed areas 58 may be altered according to the surgical procedure utilized.

Cuffs 60 also act to isolate and protect adjacent tissue from the area of circumferential burning as earlier indicated. The direction of a circumferential laser emission at target site causes vaporization of tissue and creates smoke and gases which are preferably directed away from adjacent tissues and body cavities.

Figure 6:
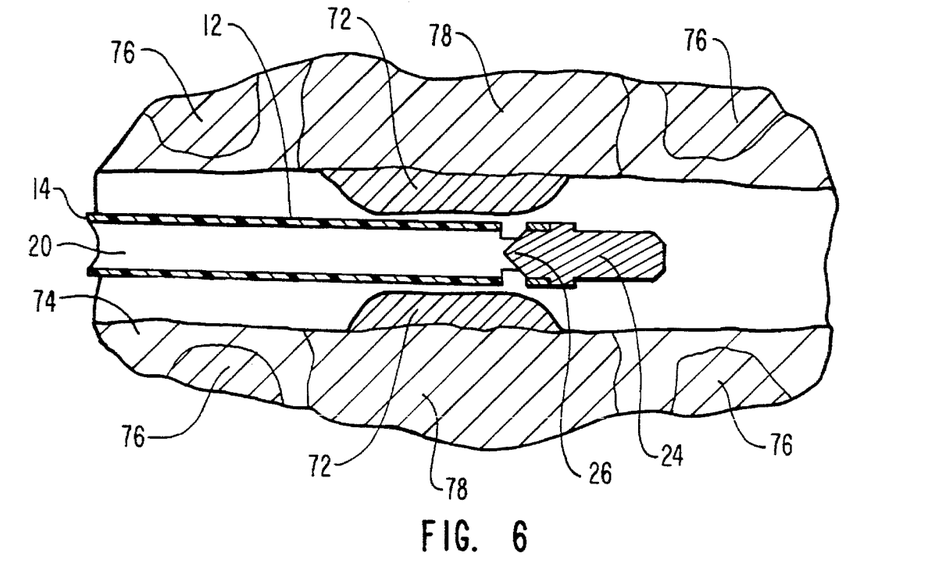
FIG. 6 is a longitudinal section of the laser probe advanced to a position between the external and internal prostatic sphincter muscles.
Figure 6A:
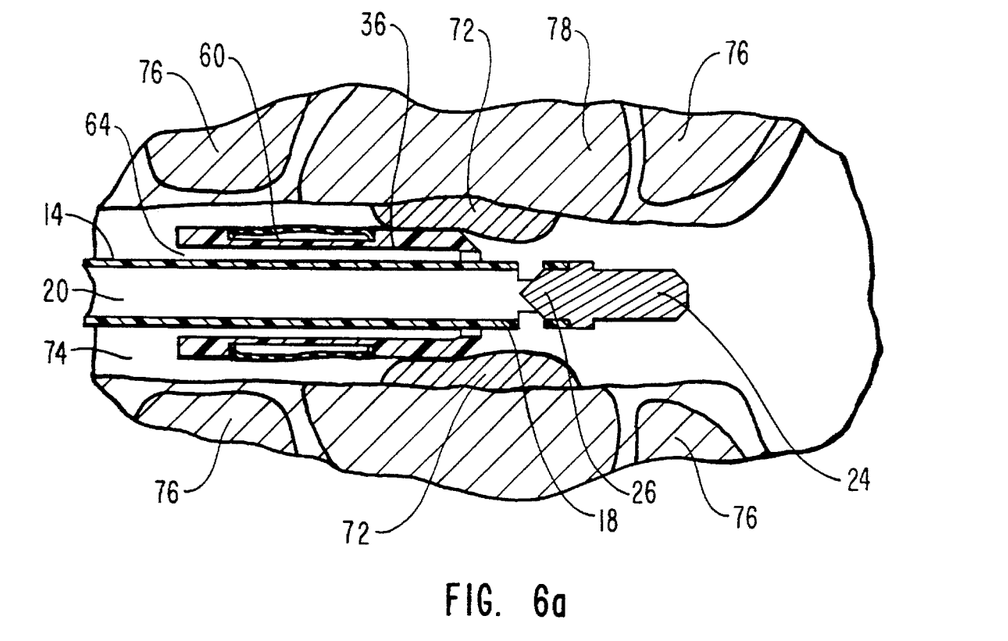
FIG. 6a is a longitudinal section of the placement device advanced to a position about the laser probe.
Figure 6B:
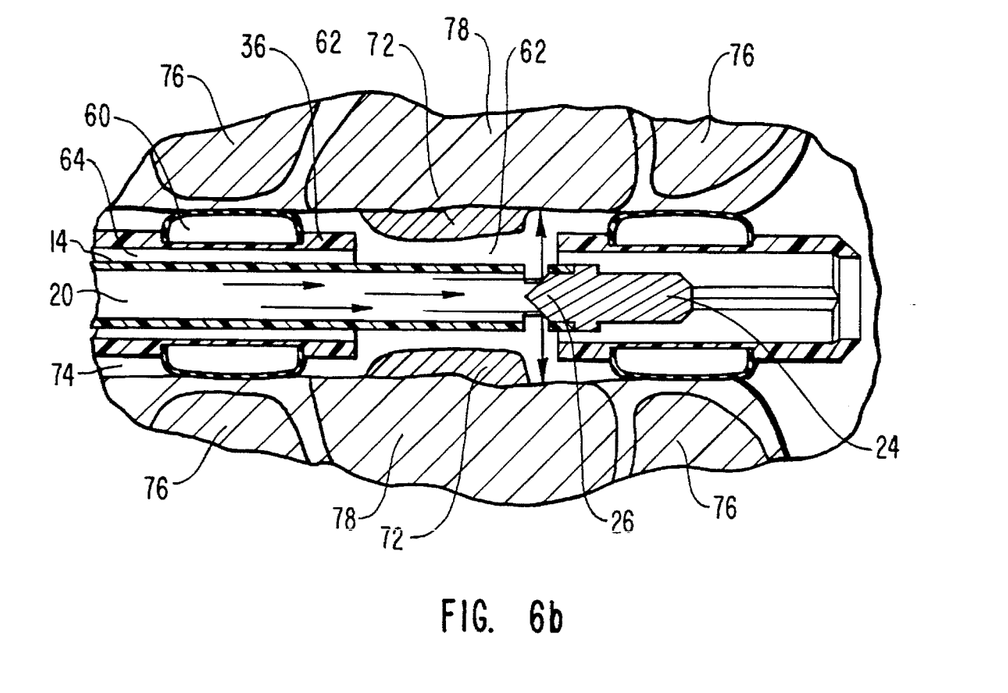
FIG. 6b is a longitudinal section of the laser light being circumferentially redirected about the laser probe, and accessing an area of adenomous tissue through the window of the placement device.

As shown in FIGS. 6b, two cuffs 60 in an inflated condition define a cavity 62 existing between placement device 36 and surrounding target tissue areas, cavity 62 being isolated from the remainder of the prostatic urethra by cuffs 60. As the circumferential laser light is redirected to target tissue areas 72, resulting in the vaporization of that tissue, smoke and gases are contained in cavity 62. The smoke and gases may be removed from cavity 62 during the surgical procedure by an evacuation means to be discussed below.

The placement means further comprises fluid transport means for channeling fluid along the placement means for inflating the inflatable cuff means such that the placement means may be secured to the body cavity adjacent the target site while simultaneously isolating the target site from adjacent tissue. Although the present invention may be embodied in other specific forms without departing from its spirit or essential characteristics, the fluid transport means comprises at least one lumen 64 extending substantially throughout the placement means, the at least one lumen communicating between an area exterior to the body cavity and the inflatable cuff means.

As shown in FIGS. 2 and 3a, at least one lumen 64 defines an internal inlet passage throughout substantially the entire length of placement device 36. Two lumens 64 are radially displaced by about 180°; however, they could be displaced to a greater or lesser extent. Lumens 64 are provided so that fluid, such as gases or liquids, may travel through placement device 36 to perform the various functions.

One such function is that fluid, such as gas or liquid, travel along lumens 64 of placement device 36 to inflate or deflate cuffs 60. The fluid travels to or from a reservoir and may be pressurized. In order for cuffs 60 to inflate or deflate it must be understood that cuffs 60 communicate with lumens 64 such that fluid flow therebetween may be accomplished as shown in FIG. 3. Although not shown, cuffs 60 have a valve through which cuffs 60 are inflated, the valve communicating with the lumens 64.

Another function of the lumens 64 is to facilitate cooling of placement device 36. Heat generated at the site of circumferential burning may be conducted away from the material comprising placement device 36 to the fluid in lumens 64. By circulating the fluid between placement device 36 and an area exterior to placement device 36 and laser probe 12, heated fluid at the site of circumferential burning may be replaced by cooled fluid to reduce the amount of heat present at the lasing site 72. Cuffs 60 are therefore cooled to decrease the temperature of the tissue area which they contact, and to prevent thermal tolerancing of the treatment site. The coolant or fluid is transmitted to the lasing site via lumens 64, from a conventional coolant reservoir, fluid pump, a heat sink, a radiator, and a fan (not shown) all contained within the laser delivery system.

Figure 6C:
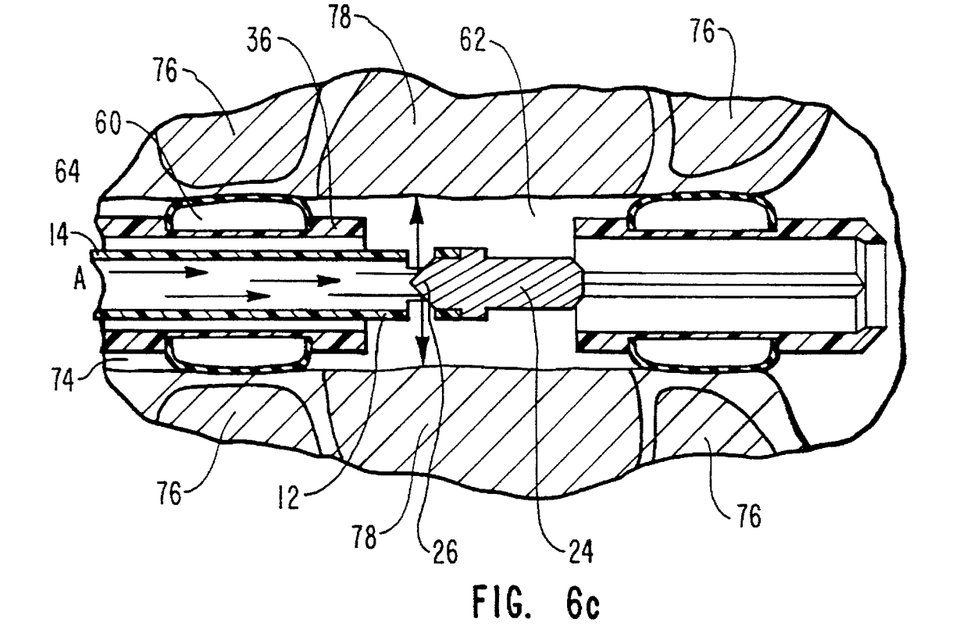
FIG. 6c is a longitudinal section of the resected area of adenomous tissue as the laser probe is retrogressively drawn through the prostatic urethra.
Figure 6D:
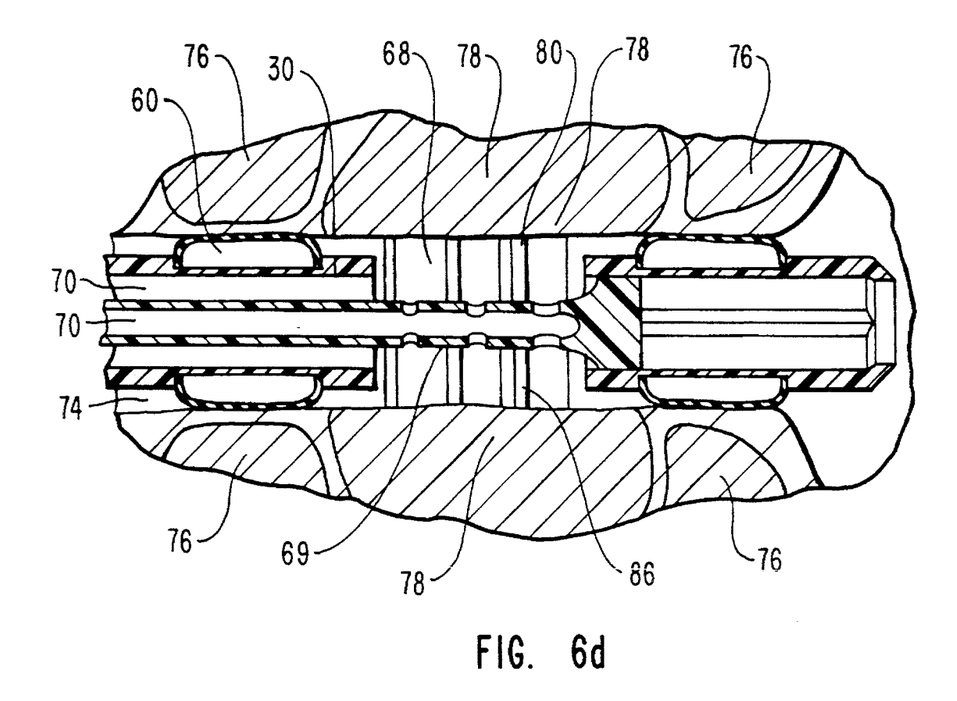
FIG. 6d is a longitudinal section of the irrigation probe retrogressively drawn through the prostatic urethra.

The present invention further comprises irrigation means for cleaning the target site 72 onto which the laser light was redirected and removing debris from the vaporization or surgical removal and cutting of tissue. As shown in FIGS. 6c and 6d, laser probe 12 may be removed from placement device 36, and replaced by an irrigation wand 68. Irrigation wand 68 is comprised of a tube 69 capable of having a plurality of irrigating lumens 70 through which fluid is transmitted to the lasing site 72 and the contaminated fluid is thereby aspirated from the lasing site 72, as illustrated in FIG. 6b. Irrigation wand 68 may be connected to a pressurized fluid source (not shown). Alternatively, other means of irrigating lasing site 72, known to those skilled in the art, may also be employed.

According to the present invention, a method for using a laser device is also provided. The method of directing laser light through laser probe 12 located adjacent target site 72 in a body cavity comprises the step of guiding laser light along a pathway through the body cavity, the pathway being defined by laser probe 12 inserted into the body cavity. In the preferred embodiment of the present invention, the laser device is inserted along the urethra 74 to perform the transurethral resection of benign prostatic hypertrophy. Alternatively, laser probe 12 could be inserted along the intravenous system to perform angioplasty or other types of body cavities.

The method further comprises the step of redirecting the laser light so that the laser light is directed onto target site 72 in a direction that is defined by a selected angle of incidence relative to the pathway and that is generally annular about substantially the entire periphery of laser probe 12. The step of redirecting comprises the step of reflecting the laser light from cone 26 to target site 72.

With regard to use of the method for transurethral resection, a patient is first placed in the lithotomy position. The laser is positioned between and below the patient's knees with the laser tube facing away from the surgeon. As illustrated in FIGS. 6 and 4b, laser probe 12, connected to a laser light generator source 6, power supply, fluid system, and control electronics, is inserted by hand into prostatic urethra 74. It is anticipated that local anaesthesia will usually be required, but that dilation will not. The advancement of laser probe 12 into urethra 74 is monitored and thereby the location of the internal/external sphincter muscles 76 together with the verumontanum will be established. The prostate gland 78 may be mapped in its entirety by taking radial soundings along the entire horizontal axis which encompasses both the internal and external sphincter 76. The distance between the two sphincter muscles 76 may be established directly from calibration marks along laser probe 12.

Placement device 36 of corresponding dimension between cuffs 60 is selected from a surgical kit. The interconnects between the laser probe 12 and laser light generator source 6 are momentarily detached while placement device 36 is threaded over laser probe 12, as shown in FIG. 6a, and then are reconnected once placement device 36 is correctly positioned. Placement device 36 is now attached to power, fluid and control electronics 8 from the laser light generator source 6 and is advanced into the prostatic urethra 74 until inflatable cuffs 60 are centered about the sphincter muscles 76, as shown in FIG. 6a. Centering of cuffs 60 about sphincter muscles 76 may be determined by directly relating positioning of placement device 36 with reference to markings along laser probe 12.

Essentially, described herein is a cuff 60 placement method which uses laser probe 12 as a guide wire to minimize the number of insertion/withdrawal cycles during any one surgical procedure. Placement device 36 may just as easily be positioned correctly along with laser probe 12.

When the correct location is established, cuffs 60 are inflated to a pressure, not damaging to tissue but sufficient to hold the placement device 36 in place as shown in FIG. 6a. As discussed, cuffs 60 may be inflated with fluid, such as a gas or liquid. The gas or liquid may be circulated between cuffs 60 to an exterior location along lumens 64 to establish a means for cooling at the location where cuffs 60 are inflated.

Laser probe 12 is then withdrawn so that it may be connected to the motor-driven focus tube (not shown). The surgery may now proceed under the control of the surgeon's hand. Super-cooled cuffs 60 establish the boundaries of the surgical site while, at the same time, protecting sphincter muscles 76.

Laser probe 12 is then advanced to the most distal point of travel as defined by inflatable cuffs 60 of placement device 36. Correct positioning of laser probe 12 is monitored by appropriate means. The surgical procedure is preferably "retrogressive"; that is, the circumferential burning laser is now activated and creating a circumferential burn within the prostatic urethra 74 and is withdrawn at a controlled rate along placement device 36, as shown by FIGS. 6b and 6c. Existing surgical techniques are "progressive" in nature resulting in continual blocking of a visual aid/lensing by excised/treated material and involved fluids. Nevertheless, if a surgeon should choose to employ such a method, the surgical procedure may be conducted progressively.

The cavity 62 formed within the prostatic urethra 74 by the circumferential burning laser can be profiled/sculpted in all axis by the adjustment of procedure parameters, i.e., laser power, axial increment, radial segment and lasing time.

When a complete "pass" has been made between cuffs 60, the surgical area is reviewed to assess whether additional passes are required. The ablated tissue/adenoma 72 will be carbonized at its surface/boundary, and will resist additional lasing; that is, it will require a greater power density to remove further material and therefore may require cleansing before the treatment can proceed. Laser probe 12 will be removed from placement device 36, disconnected from the motordriven focus tube and replaced by irrigation wand 68 which, in turn, is advanced along placement device 36 to the surgical site as shown in FIG. 6d. As in the treatment process, the cleansing procedure may be "retrogressive." Thermoplastic hairs/brush element 80 rotate about the axis of irrigation wand 68, while at the same time the carbonized surface of the surgical site is being sprayed with jets of coolant/water emanating from the probe core.

The foregoing method, directed to the transurethral resection of benign prostatic hypertrophy, is not the only method wherein the present invention may be employed. The circumferential burning laser may be employed in other surgical procedures. Above all else, procedures wherein polarized, circumferentially-radiating laser light having a high efficiency level is desired may employ the present invention. Power levels, the angle at which the circumferentially-generated light is directed, the amount of circumferentially-generated light allowed to contact tissue through the housing surrounding the laser and the like, are all factors which may be altered for a given type of surgical procedure.

An example of another area wherein the circumferentially burning laser may be used is angioplasty. The circumferential burning laser is used to vaporize plaque in vessels by burning it at levels which will not destroy the vessel, but yet will actually remove the plaque. The use of the present invention in angioplasty is beneficial because the circumferential laser may be placed in a vessel and allowed to circumferentially vaporize plaque without having to revolve the laser device. The laser is simply passed through the vessel, progressively or retrogressively.

SUMMARY

From the foregoing, the methods and apparatus of the present invention particularly facilitate a significant departure from the traditional laser apparatus of the prior art. It will be appreciated that the present invention provides apparatus and methods for a circumferential burning laser and methods for using a circumferential burning laser wherein laser energy is simultaneously directed circumferentially about a laser to affect many target sites.

Additionally, the present invention provides apparatus and methods for using a circumferential burning laser wherein laser energy is simultaneously directed circumferentially about a laser to affect a virtually circumferential target site without continuous movement of a laser which could unnecessarily injure a patient.

The present invention also provides apparatus and methods for a circumferential burning laser and methods for using a circumferential burning laser wherein laser energy is simultaneously directed circumferentially about a laser in an energy-efficient manner.

The present invention further provides apparatus and methods for a circumferential laser and methods for using a circumferential laser which will improve surgical procedures directed to the transurethral resection of benign prostatic hypertrophy.

Still further, the present invention provides apparatus and methods for a circumferential laser which will improve surgical procedures wherein the sphincter muscles of the urethra are protected from urethral surgical procedures.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A laser apparatus for placement into a body cavity and for redirecting laser light at a target site, the target site being comprised of body tissue or the like that is circumferentially located about the laser apparatus, the laser apparatus comprising:
   a probe means for insertion and placement comprising: lightguide means for guiding laser light along a pathway to a distal end of the lightguide means;
   tip means, joined to the lightguide means at the distal end thereof, for redirecting the laser light onto the target site but without focusing it such that the redirected laser light contacts the circumferentially located target site about substantially its entire periphery in a substantially continuous and uninterrupted annular pattern of substantially uniform power distribution; and
   placement means surrounding the probe means for supporting the probe means and for simultaneously isolating the target site from adjacent body tissue so as to protect the tissue from increased thermal conditions while laser light is directed through the laser probe, and wherein the placement means comprises window mean for allowing the redirected laser light to reach the target site through the placement means.

2. A laser apparatus as defined in claim 1, wherein the placement means comprises a tube having a proximal end and a distal end and through which the probe means slidably moves.

3. A laser apparatus as defined in claim 1, wherein the placement means comprises inflatable cuff means for securing the placement means adjacent the target site while simultaneously isolating the target site from adjacent tissue.

4. A laser apparatus as defined in claim 3, wherein the inflatable cuff means comprises at least one recessed area along the placement means, and at least one inflatable cuff residing therein to secure the placement means to tissue area when the at least one inflatable cuff is in an inflated condition.

5. A laser apparatus as defined in claim 3, wherein the placement means comprises fluid transport means for channeling fluid along the placement means for conducting said fluid to the inflatable cuff means such that the cuff means is inflatable by entry of said fluid into the cuff means.

6. A laser apparatus as defined in claim 5, wherein the fluid transport means comprises at least one lumen extending substantially throughout the placement means, the at least one lumen communicating between an area exterior to the body cavity and the inflatable cuff means.

7. A laser apparatus as defined in claim 1, further comprising alignment means for aligning and for supporting the probe means within the placement means.

8. A laser apparatus as defined in claim 7, wherein the alignment means comprises a track along which the probe means is aligned and slidably moved in relation to the target site.

9. A laser apparatus as defined in claim 8, wherein the track comprises:
   a plurality of longitudinally placed ridges formed along the placement means; and
   a plurality of longitudinally placed recesses formed along the probe means that slidingly receive and engage said ridges.

10. A laser apparatus as defined in claim 1, wherein the placement means comprises a first window means for allowing the redirected laser light to reach the target site through the placement means.

11. A laser apparatus as defined in claim 10, wherein the first window means comprises at least one window formed in the placement means to provide an opening between the target site and the tip means from which the laser light is redirected from the probe means.

12. A laser apparatus as defined in claim 1, wherein the placement means comprises bore means for providing an area through which the probe means is slidably movable such that the probe means is uninterrupted by the tissue area.

13. A laser apparatus as defined in claim 12, wherein the bore means comprises a longitudinal bore extending along the placement means, the bore configured such that the probe means may move slidably throughout the bore.

14. A laser apparatus as defined in claim 1, wherein the lightguide means comprises a lightguide to support the tip means in a position to receive the laser light guided along the pathway defined by the lightguide.

15. A laser apparatus as defined in claim 14, wherein the lightguide comprises a ceramic cylinder extending in a longitudinal axis, the tip means being positioned in a cavity within the cylinder.

16. A laser apparatus as defined in claim 15, wherein the lightguide comprises window means for allowing the redirected laser light to reach the target site from the tip means positioned in the cylindrical cavity.

17. A laser apparatus as defined in claim 16, wherein the window means comprises at least one window to allow the redirected light to unobstructively travel between the tip means present in the cylindrical cavity to the target site.

18. A laser apparatus as defined in claim 1, wherein said placement means further comprises irrigation means longitudinally extending to the target site for cleaning the target site onto which the laser light is directed.

19. A laser apparatus as defined in claim 18, wherein the irrigation means comprises means connected by a tube to a pressurized fluid source, for introducing a fluid to cleanse the target site area.

20. A laser apparatus as defined in claim 1, wherein the tip means comprises an elongated sleeve having a substantially symmetrical reflective cone attached to one end thereof, the reflective cone attached to the lightguide means such that the laser light strikes the reflective surface of the cone.

21. A laser apparatus for extending through a generally tubular area and for removing excess tissue from a target site located circumferentially thereabout within the generally tubular area, the laser apparatus comprising:

a lightguide extending through the generally tubular area to the target site, the lightguide defining a pathway for laser light directed therethrough;

an elongated sleeve having a tip attached to one end thereof, the tip comprising a substantially symmetrical reflective conical surface that receives and redirects the laser light, the conical surface being defined by selected angle of incidence relative to the pathway defined by the lightguide so that the laser light striking the reflective conical surface is redirected generally annularly about substantially the entire periphery of the tip onto the target site circumferentially located thereabout to remove the excess tissue; and a placement tube having a proximal end and a distal end, and at least one lumen, at least one area along the exterior of the placement tube being recessed and communicating with the at least one lumen, the placement tube further comprising at least one inflatable cuff residing in the at least one recessed area, the at least one inflatable cuff securing the placement tube adjacent the target site while simultaneously isolating the target site from adjacent tissue when in an inflated condition, the at least one inflatable cuff communicating with the at least one lumen to channel fluid between the at least one lumen and the at least one inflatable cuff to cool and inflate the at least one inflatable cuff, the placement tube having a bore through which the lightguide slidably engages, the bore being accessible to the generally tubular area about the placement tube through at least one window formed in the placement tube, the window providing access about the placement tube so as to allow the laser light to contact the target site as the laser light travels from the reflective conical surface through the at least one window of the placement tube to the target site, and the placement tube further comprising at least one longitudinally placed ridge to align the lightguide to the placement tube when inserted therein, and the lightguide further comprising at least one longitudinally placed recess at its perimeter which communicates with the at least one ridge of the placement tube such that the lightguide is aligned when inserted within the placement tube.

22. A laser apparatus as defined in claim 21, wherein the reflective conical surface is comprised of gold plated metal.

23. A laser apparatus as defined in claim 21, wherein the reflective conical surface is comprised of a Germanium reflector.

24. A laser apparatus as defined in claim 21, wherein the bore in the placement tube is centrally located.

25. A laser apparatus as defined in claim 21, wherein the placement tube is comprised of two lumen extending substantially throughout placement tube, the two lumen being radially displaced from one another.

26. A laser apparatus as defined in claim 21, wherein the at least one inflatable cuff has a valve through which the at least one inflatable cuff is inflated, the valve communicating with the at least one lumen of the placement tube.

27. A laser apparatus as defined in claim 21, wherein the at least one lumen provides a route through which fluid travels to enter and inflate the at least one inflatable cuff.

28. A laser apparatus as defined in claim 21, wherein the fluid which travels through the at least one lumen is capable of cooling placement tube as the fluid travels therethrough.

29. A laser apparatus as defined in claim 21, wherein the lightguide is produced of ceramics having a concentric bore.

30. A laser apparatus as defined in claim 21, wherein the laser light traveling along the pathway to strike the surface of the reflective cone is a $TE_{\phi 1}$ emission.

31. A method of directing laser light through a laser probe located adjacent a surrounding target site in a body cavity, the method comprising the steps of:

guiding laser light along a pathway, the pathway being defined by a laser probe;

redirecting the laser light onto the target site but without focusing it such that the redirected laser light contacts the surrounding target site about substantially its entire periphery in a substantially continuous and uninterrupted annular pattern of substantially uniform power distribution; and inserting a placement device to support the laser probe and to isolate the target site from adjacent body tissue so as to protect the tissue from increased thermal conditions while laser light is directed through the laser probe, and directing the redirected laser light to the target site through a window in the placement device.

32. The method of directing laser light as defined in claim 31, wherein the method of inserting a placement device comprises the step of inflating at least one cuff between the tissue and the placement device.

33. The method of directing laser light as defined in claim 32, wherein the step of inflating at least one cuff comprises the step of channeling fluid to the at least one cuff.

34. The method of directing laser light as defined in claim 33, wherein the step of channeling fluid comprises the step of introducing fluid that can cool the pathway as the cooling fluid is channeled to the at least one cuff.

35. The method of directing laser light as defined in claim 31, wherein the method further comprises the step of moving the laser probe along the pathway so that the laser light is directed onto the target site over a region corresponding to the distance travelled by the laser probe.

36. The method of directing laser light as defined in claim 35, wherein the step of moving the laser probe comprises the step of moving the laser probe slidably through the placement device.

37. The method of directing laser light as defined in claim 35, wherein the step of moving the laser probe comprises the step of retrogressively drawing the laser probe along the pathway to direct the laser light onto the target site.

38. The method of directing laser light as defined in claim 35, wherein the step of moving the laser probe comprises the step of progressively moving the laser probe along the pathway to direct the laser light onto the target site.

39. The method of directing laser light as defined in claim 35, wherein the step of moving the laser probe comprises the step of repeating to move the laser probe along the pathway so that the laser light is frequently directed onto the target site region.

40. The method of directing laser light as defined in claim 31, wherein the step of redirecting laser light onto the target site comprises the step of ablating the target site from adjacent tissue areas.

41. The method of directing laser light as defined in claim 31, wherein the step of redirecting laser light comprises the step of reflecting the laser light from a conical surface of an elongated sleeve of the laser probe to the target site.

42. The method of directing laser light as defined in claim 41, wherein the step of reflecting the laser light comprises the step of adjusting the angle of incidence of the conical surface of the elongated sleeve relative to the pathway to redirect laser light onto the target site in a direction that is defined by the adjusted angle of incidence relative to the pathway.

43. The method of directing laser light as defined in claim 42, wherein the step of adjusting the angle of incidence of the conical surface of the elongated sleeve relative to the pathway comprises the step of replacing a first elongated sleeve having a first angle of incidence with a second elongated sleeve having a second and different angle of incidence.

44. The method of directing laser light as defined in claim 31, wherein the method further comprises the step of irrigating the target site so that the target site may be cleaned.

* * * * *